United States Patent [19]
Hupe et al.

[11] Patent Number: 5,516,807
[45] Date of Patent: May 14, 1996

[54] METHOD FOR TREATING VASCULAR PROLIFERATIVE DISORDERS FOLLOWING BALLOON ANGIOPLASTY

[75] Inventors: Donald Hupe; Joan A. Keiser, both of Ann Arbor, Mich.

[73] Assignee: Warner-Lambert Company, Morris Plains, N.J.

[21] Appl. No.: 329,588

[22] Filed: Oct. 25, 1994

[51] Int. Cl.⁶ .................................................. A61K 31/13
[52] U.S. Cl. ........................................ 514/673; 514/663
[58] Field of Search ...................................... 514/663, 673

[56] References Cited

U.S. PATENT DOCUMENTS 4,507,321  3/1985  Raisfeld ................................ 514/673

FOREIGN PATENT DOCUMENTS

| | | |
|---|---|---|
| 0162413 | 11/1985 | European Pat. Off. . |
| 0277635 | 8/1988 | European Pat. Off. . |
| 0349224 | 1/1990 | European Pat. Off. . |
| 0399519 | 11/1990 | European Pat. Off. . |
| 52-118405 | 10/1977 | Japan . |
| 60-6348 | 2/1985 | Japan . |

OTHER PUBLICATIONS

Endean, et al., *Journal of Surgical Research*, 50:634–637 (1991).

*Primary Examiner*—T. J. Criares
*Attorney, Agent, or Firm*—Charles W. Ashbrook

[57] ABSTRACT

Polyamines inhibit vascular smooth muscle proliferation and thus are useful in treating and preventing vascular proliferative disorders such as restenosis following balloon angioplasty.

10 Claims, 1 Drawing Sheet

METHOD FOR TREATING VASCULAR PROLIFERATIVE DISORDERS FOLLOWING BALLOON ANGIOPLASTY

FIELD OF THE INVENTION

This invention concerns a method for treating and preventing vascular proliferative disorders such as restenosis following coronary angioplasty.

BACKGROUND OF THE INVENTION

Vascular proliferative disorders are conditions within the walls of blood vessels, including arteries and veins, which result in occlusion or blockage of blood flow. A common vascular proliferative disorder is restenosis. Restenosis is a major clinical problem associated with coronary angioplasty. Restenosis generally occurs within about 0 to 6 months in about 30% to 50% of patients who undergo balloon angioplasty to clear clogged coronary arteries in an effort to prevent and treat heart disease due to occluded arteries. The resulting restenosis causes substantial patient morbidity and health care expenses.

The process of restenosis is initiated by injury of the vessel, with the subsequent release of thrombogenic, vasoactive, and mitogenic factors. Endothelial and deep-vessel injury leads to platelet aggregation, thrombus formation, inflammation, and activation of macrophages and smooth-muscle cells. These events induce the production and release of growth factors and cytokines, which in turn may promote their own synthesis and release from target cells. Thus, a self-perpetuating process is initiated.

There currently are no effective treatments available for restenosis. Accordingly, a major medical need exists for effective treatments for restenosis and other vascular proliferative disorders.

We have now discovered that certain polyamines are effective for inhibiting vascular smooth muscle proliferation, and as such are useful in treating and preventing vascular proliferative disorders such as restenosis. There are numerous polyamines known in the art. Many are under active investigation as potential treatments for neoplastic and viral diseases. For example, EP 0349,224 describes a series of polyamines related to spermine, spermidine, norspermidine, homospermidine, and putrescine (1,4-diaminobutane). The compounds are said to be anti-neoplastics, antivirals, anti-retrovirals, and anti-psoriasis agents. Similarly, EP 0277,635 describes the synthesis of certain polyamines which are said to be useful for treating diseases caused by infestation with a variety of parasitic protozoa. EP 0399,519 describes the use of certain polyamines to potentiate cell-mediated immunity. EP 0162,413 discloses polyamines for use in treating neoplasms. U.S. Pat. No. 4,507,321 describes the use of polyamines to stimulate epithelial cell regrowth for wound healing. Japanese Patent No. 85/6348 describes several new polyamines for use in cell proliferation.

Endean, et al., in *J. Surgical Research*, 50:634–637 (1991) discloses that polyamines which exist in biological systems are synthesized from ornithine through the action of ornithine decarboxylase. The authors describe experiments to block the activity of this enzyme, thereby reducing polyamine synthesis, thus inhibiting the formation of intimal hyperplasia, which is said to be a significant cause of restenosis. It has also been demonstrated that certain polyamine analogs, including the compounds described in this application, are effective agents for inducing the transcription of spermine-spermidine acyltransferase, or SSAT. SSAT is an important enzyme in the regulation of pool sizes of polyamines, and induction of this enzyme increases the rate at which polyamines are metabolized and removed from the cell, thereby depleting their levels. This is an effective method for inhibiting proliferation of, for example, cancer cells, as taught by Fogel-Petrovic M; Shappell NW; Bergeron, R. J.; Porter, C. W., *J. Biol. Chem.* 7(8):653–61 (1993).

An object of this invention is to provide a method for treating and preventing proliferative vascular disorders, such as restenosis associated with angioplasty.

SUMMARY OF THE INVENTION

This invention relates to a method for treating and preventing vascular proliferative disorders, especially restenosis following balloon angioplasty. More particularly, the invention provides a method for treating and preventing vascular proliferative disorders comprising administering to a subject in need of treatment an effective amount of a polyamine defined by the formula $$R_1-N^1-(CH_2)_m-N^2-(CH_2)_n-N^3-(CH_2)_m-N^4-R_6$$
$$\phantom{R_1-N^1}\Big|\phantom{-(CH_2)_m-N^2}\Big|\phantom{-(CH_2)_n-N^3}\Big|\phantom{-(CH_2)_m-N^4}\Big|$$
$$\phantom{R_1-N^1-}R_2\phantom{(CH_2)_m-}R_3\phantom{-(CH_2)_n-}R_4\phantom{-(CH_2)_m-}R_5$$

wherein:
$R_1$ and $R_6$ independently are hydrogen or $C_1$-$C_{12}$ alkyl;
$R_2$, $R_3$, $R_4$, and $R_5$ independently are hydrogen or $C_1$-$C_{12}$ alkyl;
m and n are integers from 3 to 6;
or a pharmaceutically acceptable salt thereof, provided that at least one of $R_1$, $R_2$, $R_5$, and $R_6$ is $C_1$-$C_{12}$ alkyl.

The method preferably is carried out utilizing polyamines of the above formula wherein $R_1$ and $R_6$ both are $C_1$-$C_6$ alkyl, especially ethyl, and $R_2$ and $R_5$ both are hydrogen. The method is ideally carried out utilizing a compound of the formula

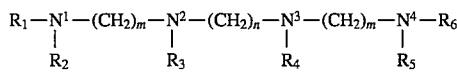

where n is 3 or 4.

The method is especially preferred utilizing the following compounds:
bis ethyl spermine (e.g., $N^1,N^{12}$-diethylspermine, where n is 4, BES); and
bis ethyl norspermine (e.g., $N^1, N^{11}$-diethylnorspermine, where n is 3,BENSPM).

Another preferred embodiment utilizes compounds of the formula

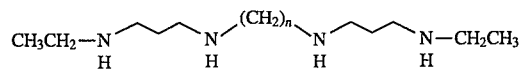

especially
bis ethyl homospermine (e.g., $N^1,N^{14}$-diethylhomospermine, where n is 4,BEHNS).

A preferred treatment comprises administering a polyamine to a patient suffering from or susceptible to restenosis following angioplasty. Another preferred treatment comprises administering a polyamine to a subject suffering from a vascular proliferative disorder following implantation of a graft or shunt. Still another preferred method involves treating or preventing a vascular proliferative disorder in a subject undergoing atherectomy.

DETAILED DESCRIPTION OF THE INVENTION

Figure 1:
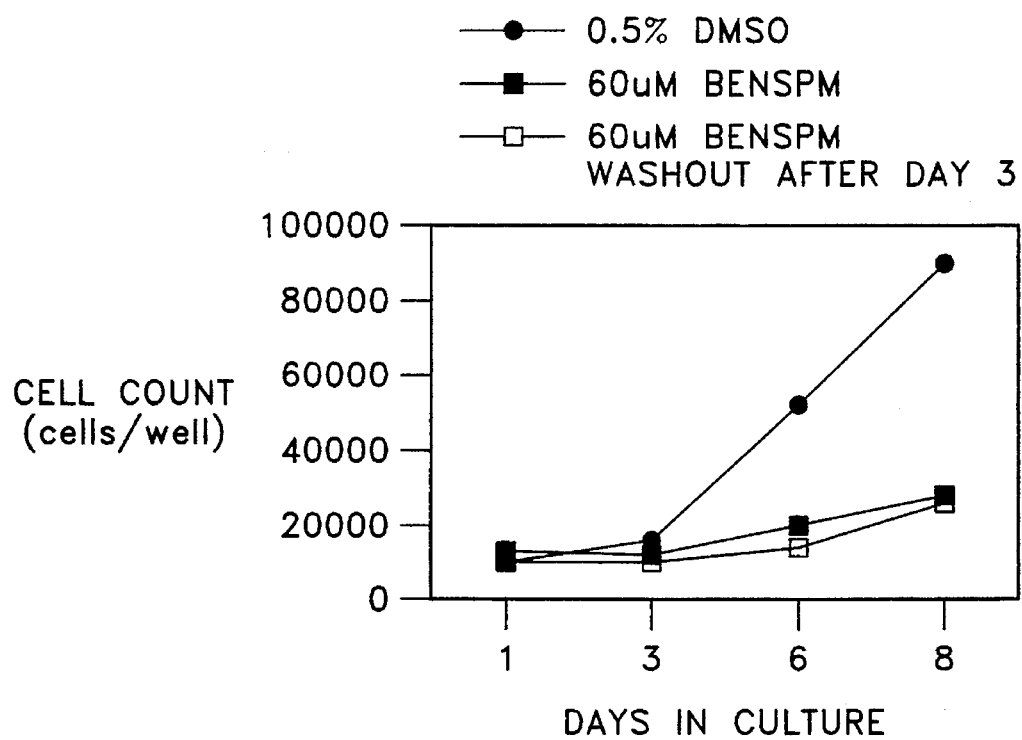
FIG. 1 shows the ability of one polyamine known as BENSPM to inhibit proliferation of vascular smooth muscle cells in vitro over an 8-day period.

As used herein, the term "vascular proliferative disorder" means a condition within the walls of blood vessels, including arteries and veins, which result in occlusion of blockage of blood flow. These conditions generally result from injuries and wall alterations incurred during surgical intervention, for example during angioplasty, atherectomy, graft or shunt implantion, coronary by-pass surgery, and the like. A common vascular proliferative disorder is restenosis that often occurs in patients undergoing percintaneous transluminal coronary angioplasty. The chief limitation to long-term, event-free survival of patients who have undergone angioplasty is the recurrence of the stenosis, i.e., restenosis. Other surgical procedures which commonly lead to vascular proliferative disorders include atherectomies, as well as graft or shunt implantations. This invention provides a method for preventing and treating such vascular proliferative disorders.

The compounds to be utilized in this invention are known and are readily prepared by any of several art-recognized methods. For example, Bergeron, in U.S. Pat. No. 5,091,576, describes a wide variety of polyamines such as those required for the present method. Synthesis of specific compounds to be utilized in this invention are provided by Bergeron, et al., in *J. Med. Chem.*, 31:1183–1190 (1988). A typical synthesis involves first monosulfonating all of the polyamine nitrogen atoms with p-toluenesulfonyl chloride, thereby leaving only the terminal nitrogens to be alkylated. The resulting sulfonamides were reacted with sodium hydride in an organic solvent such as dimethylsulfoxide, and reacted with an alkylating agent, for instance, methyl iodide, ethyl iodide, or the like. The terminally dialkylated sulfonamides thus formed are next hydrolyzed to remove sulfonyl protecting groups, for example, by reaction with sodium in liquid ammonia. The polyamines thus formed are purified by routine methods, for instance, by forming an acid addition salt such as the hydrochloride, and crystallizing it from common solvents. The salts can be utilized in the present method, or can be hydrolyzed with a base such as sodium hydroxide to give the free polyamine.

The polyamines are preferably formulated with common pharmaceutical carriers and excipients for use in the method of this invention. Typical formulations will contain from about 0.05% to about 95.0% by weight of polyamine, ideally from about 1.0% to about 50% by weight. The polyamines will be admixed with common excipients and carriers such as waxes, vegetable oils, gelatins, gums, petrolatum, mineral oil, microcrystalline cellulose, polyethylene, and copolymers such as lactic-glycolic copolymers, starch, and the like. The compositions can be formulated for convenient oral or parenteral administration. The compounds can also be impregnated onto sutures and polymeric resins and attached or wrapped directly to or around the artery at the site of injury, thereby providing intermediate and sustained release of the polyamine at the locus in need of treatment. In a preferred embodiment, the compounds will be formulated for delivery via a catheter or the like directly to the locus of the restenosis.

The polyamines will be administered in an amount that is effective in preventing or treating a vascular proliferative disorder, thereby restoring blood flow to the extent required for normal functioning.

The effective amount of polyamine to be administered to a subject will be from about 20 to about 200 mg/kg of body weight, preferably from about 25 mg/kg to about 75 mg/kg. The compounds can be administered orally in the form of tablets, capsules, emulsions, solutions, suspensions, and the like. The compounds can be administered parenterally, for instance intravenously or by intramuscular or subcutaneous injection, in common diluents such as isotonic saline or 0.5% sterile glucose. The compounds can be formulated with waxes for use as suppositories. The compounds can also be formulated for transdermal delivery, for instance as a patch applied near the vascular area to be treated. The compounds can be administered prior to initiation of the stenosis, for example prior to surgery, or at the same time as the surgery, or periodically following the vascular proliferative disorder.

The ability of the polyamines described herein to prevent and treat restenosis following angioplasty has been demonstrated in tests designed to establish such utility. For example, bis ethyl norspermine (BENSPM) was shown to significantly inhibit the growth of rat aortic smooth muscle cells for up to 15 days following a single dosing. In this test, rat aortic smooth muscle cells (RASMC) were plated into a 24-well plate (10,000 cells per well) in Dulbecco's modified Eagle's medium (DMEM) with 10% v/v fetal bovine serum (FBS). Cells were maintained in DMEM/10% FBS throughout the experiment. After a 24-hour attachment period, vehicle (50% v/v dimethylsulfoxide [DMSO] in water) was added to half the wells (final concentration of DMSO in the culture was 0.5%), and BENSPM (final conc 60 μm in the well) in vehicle was added to the other half of the wells. Cells were counted using an automated cell counter (Coulter Electronics, Miami Lakes, Fla.) after Days 1, 3, 6, 8, 10, and 15. The control group of cells were exposed to vehicle only through Day 8. A second group received 10% FBS and BENSPM at 60 μm throughout the entire study. A third group of cells was exposed to 60 μm of BENSPM for Days 1 to 6, and then exposed to DMEM plus 10% FBS for Days 7 to 15. Triplicate determinations were made for each data point.

Figure 2:
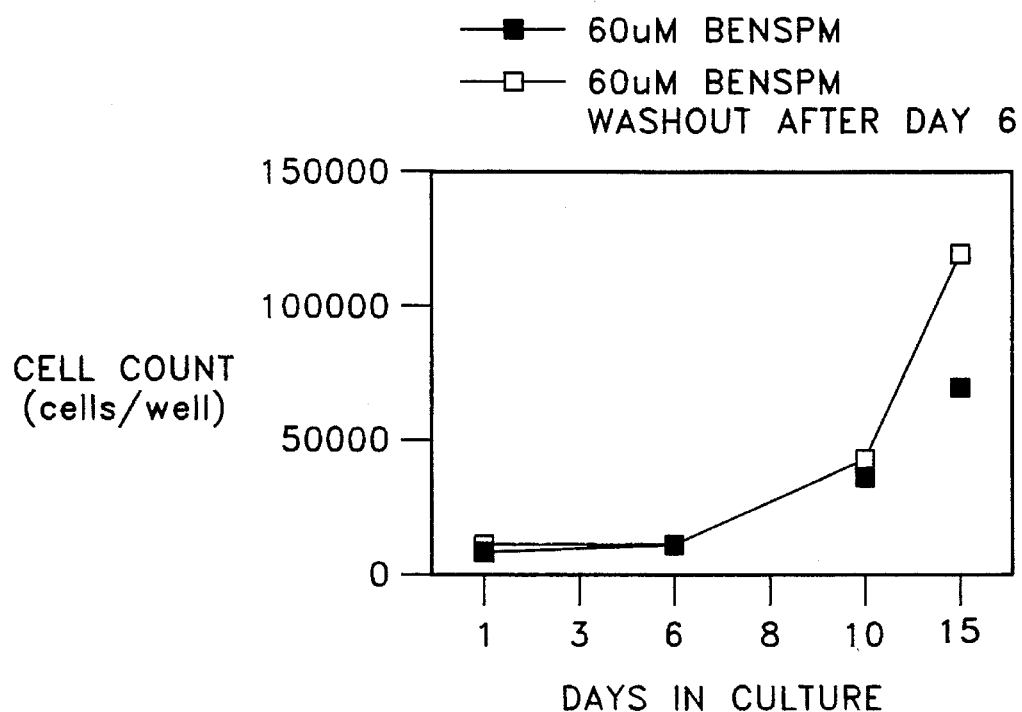
FIG. 2 shows the antiproliferative activity of a polyamine over a 15-day period, and the continued antiproliferative effects following withdrawal of the polyamine.

The results of these tests are presented in FIGS. 1 and 2. FIG. 1 shows the inhibitory effects of BENSPM at 60 μm over an 8-day period. BENSPM inhibited RASMC growth for the entire 8-day period. At Day 8, BENSPM inhibited RASMC growth by 68% compared to vehicle alone. FIG. 1 additionally establishes that when BENSPM was washed out of certain wells, the antiproliferative effect continued, such that cell growth was inhibited by 70% at Day 8.

FIG. 2 shows the effects of BENSPM on cell growth over a 15-day period. The blackened squares show that continued administration of BENSPM caused continued cell growth inhibition, and that inhibition even continued following washout of BENSPM. Specifically, a 40% reversal of the antiproliferative effects was observed on Day 15 following wash out of BENSPM on Day 6. These data establish BENSPM is effective at inhibiting smooth muscle cell growth, and thus is useful at treating and preventing restenosis.

The polyamines described herein are additionally effective when evaluated in a balloon angioplasty model in animals such as rats and rabbits. For example, the compounds are evaluated in rats according to the following protocol.

Balloon Angioplasty of Rat Carotid Arteries

Male Sprague-Dawley rats (350–450 g) are divided into two treatment groups: one group of rats (n=10) are treated with drug (100 mg/kg PO, BID). The second group receive vehicle (2 mL/kg PO, BID; n=10). All animals were pretreated for 2 days prior to surgery and continued to receive daily drug treatment post-injury until sacrificed.

Balloon injury in rat carotid arteries were performed according to the following protocol. Rats were anesthetized with Telazol (0.1 mL/100 g IM) and the carotid artery exposed via an anterior mid-line incision on the neck. The carotid artery was isolated at the bifurcation of the internal and external carotid arteries. A 2 F embolectomy catheter was inserted in the external carotid artery and advanced down the common carotid to the level of the aortic arch. The balloon was inflated, and the catheter is dragged back to the point of entry and then deflated. This procedure is repeated two more times. The embolectomy catheter was then removed, and the external carotid artery was ligated leaving flow intact through the internal carotid artery. Surgical incisions were closed, and the animal was allowed to recover from anesthesia before being returned to its home cage.

At various time points, post-injury animals were euthanized with $CO_2$ inhalation, and the carotid artery was perfusion-fixed and processed for histologic examination. Morphologic determination of lesion size was made by measuring the area of the carotid artery intima expressed as a ratio of the media in individual animals. Up to 16 sections were prepared from each animal to give a uniform representation of lesion size down the length of the carotid artery. The cross-sectional areas of the blood vessels were quantified using an image analysis program from Princeton Gamma Tech (Princeton, New Jersey).

A preferred method of treating and preventing restenosis includes delivering the polyamine at or near the site of the occlusion. Typically, the polyamine can be formulated as a liquid, paste, or gel and delivered by a catheter inside the vessel or outside. Alternatively, the polyamine can be impregnated in a suture or biodegradable resin or the like and wrapped or otherwise adhered to the outer surface of the artery.

We claim:

1. A method for treating or preventing restenosis following balloon angioplasty, restenosis following graft or shunt implantation, or restenosis following atherectomy comprising administering to a subject in need of treatment or prevention an effective amount of a polyamine of the formula

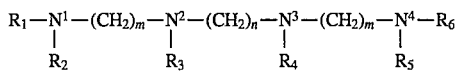

wherein:

$R_1$ and $R_6$ independently are hydrogen or $C_1$–$C_{12}$ alkyl;

$R_2$, $R_3$, $R_4$, and $R_5$ independently are hydrogen or $C_1$–$C_{12}$ alkyl;

m and n are integers from 3 to 6;

or a pharmaceutically acceptable salt thereof, provided at least one of $R_1$, $R_2$, $R_5$, and $R_6$ is $C_1$–$C_{12}$ alkyl.

2. A method according to claim 1 wherein the condition being prevented or treated is restenosis following balloon angioplasty.

3. A method of claim 1 employing a compound wherein $R_1$ and $R_6$ both are $C_1$–$C_6$ alkyl, and $R_2$ and $R_5$ both are hydrogen.

4. A method of claim 3 employing a compound wherein $R_1$ and $R_6$ both are ethyl.

5. A method of claim 4 employing a compound wherein m is 3.

6. A method of claim 5 employing a compound wherein n is 4.

7. A method of claim 5 employing a compound wherein n is 3.

8. A method of claim 4 employing a compound wherein m is 4 and n is 4.

9. A method of claim 1 wherein the condition being prevented or treated is vascular proliferative disorder following graft or shunt implantation.

10. A method of claim 1 wherein the condition being prevented or treated is vascular proliferative disorder following atherectomy.

* * * * *